United States Patent
Bilge (10) Patent No.: US 8,556,957 B2
(45) Date of Patent: Oct. 15, 2013

(54) BIODEGRADABLE MEDICAL DEVICE WITH HYDROXYAPATITE FILAMENTS AND BIODEGRADABLE POLYMER FIBERS

(75) Inventor: Iskender Bilge, San Francisco, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 699 days.

(21) Appl. No.: 12/487,327

(22) Filed: Jun. 18, 2009

(65) Prior Publication Data

US 2010/0324646 A1    Dec. 23, 2010

(51) Int. Cl.
    *A61F 2/06*     (2013.01)
    *A61L 27/32*     (2006.01)
    *D03D 9/00*     (2006.01)
    *D03D 15/00*     (2006.01)
    *D03D 19/00*     (2006.01)
    *B32B 27/04*     (2006.01)
    *B32B 27/12*     (2006.01)
    *A61F 2/00*     (2006.01)

(52) U.S. Cl.
    USPC ............ 623/1.15; 623/1.38; 427/2.27; 442/4; 442/123; 424/426

(58) Field of Classification Search
None
See application file for complete search history.

(56) References Cited

U.S. PATENT DOCUMENTS

| | | | |
|---|---|---|---|
| 7,247,288 B2 | 7/2007 | Kumta et al. | |
| 2003/0219466 A1 | 11/2003 | Kumta et al. | |
| 2005/0149102 A1 | 7/2005 | Radisch et al. | |
| 2005/0163954 A1* | 7/2005 | Shaw | 428/36.1 |
| 2005/0169959 A1 | 8/2005 | Hunter et al. | |
| 2005/0261721 A1 | 11/2005 | Radisch et al. | |
| 2006/0134160 A1 | 6/2006 | Troczynski et al. | |
| 2006/0199876 A1 | 9/2006 | Troczynski et al. | |
| 2007/0038290 A1 | 2/2007 | Hunag et al. | |
| 2007/0141111 A1* | 6/2007 | Suokas et al. | 424/426 |
| 2007/0219626 A1 | 9/2007 | Rolando et al. | |
| 2007/0232169 A1 | 10/2007 | Strickler et al. | |
| 2007/0282247 A1 | 12/2007 | Desai | |
| 2007/0282434 A1* | 12/2007 | Wang et al. | 623/1.38 |
| 2008/0275540 A1 | 11/2008 | Wen | |
| 2009/0030504 A1 | 1/2009 | Weber et al. | |
| 2009/0043380 A1* | 2/2009 | Blaha et al. | 623/1.46 |
| 2009/0143853 A1 | 6/2009 | Morris et al. | |
| 2010/0076556 A1 | 3/2010 | Tomantschger et al. | |

FOREIGN PATENT DOCUMENTS

WO    WO2005/072651    8/2005

OTHER PUBLICATIONS

Ramanan et al., "A Study of Hydroxyapatite Fibers Prepared Via Sol-Gel Route" Material Letters, 58, 2004, 3320-3323, Elsevier Pub.
Kim et al., "Poly(Lactide-Co-Glycolide)/Hydroxyapatite Composite Scaffolds for Bone Tissue Engineering" Biomaterials 27 (2006) 1399-1409, Elsevier Pub.

(Continued)

*Primary Examiner* — Andrew Iwamaye
*Assistant Examiner* — Leslie Coburn (57) ABSTRACT

A system for treating a vascular condition includes a stent including hydroxyapatite fibers interwoven to define a stent lumen. Another aspect of the invention is a method of manufacturing a stent by forming hydroxyapatite fibers and biodegradable polymeric fibers, and interweaving the fibers to form a stent wall. The hydroxyapatite fibers can be formed by a sol-gel process, followed by spinning of the gel to form the hydroxyapatite fibers.

10 Claims, 6 Drawing Sheets

(56) References Cited

OTHER PUBLICATIONS

Song, K. Chang, "Preparation of Mullite Fibers by the Sol-Gel Method" Journal of Sol-Gel Science and Technology 13, 1017-1021 (1998).

Vazquez et al., "Stoichiometric Hydroxyapatite Obtained by Precipitation and Sol Gel Processes" Investigacion, Revista Mexicana De Fisica 51 (3) 284-293, Jun. 2005.

* cited by examiner

BIODEGRADABLE MEDICAL DEVICE WITH HYDROXYAPATITE FILAMENTS AND BIODEGRADABLE POLYMER FIBERS

TECHNICAL FIELD

This invention relates generally to biomedical devices that are used for treating vascular conditions. More specifically, the invention relates to a biodegradable medical device with hydroxyapatite filaments and/or biodegradable polymer fibers.

BACKGROUND OF THE INVENTION

Stents are generally cylindrical-shaped devices that are radially expandable to hold open a segment of a vessel or other anatomical lumen after implantation into the body lumen.

Various types of stents are in use, including expandable and self-expanding stents. Expandable stents generally are conveyed to the area to be treated on balloon catheters or other expandable devices. For insertion into the body, the stent is positioned in a compressed configuration on the delivery device. For example, the stent may be crimped onto a balloon that is folded or otherwise wrapped about the distal portion of a catheter body that is part of the delivery device. After the stent is positioned across the lesion, the balloon is expanded by the delivery device, causing the diameter of the stent to expand. For a self-expanding stent, a sheath covering the stent is retracted allowing the unconstrained stent to expand, the physiological conditions at the placement site cause the stent to expand, or the combination causes the stent to expand.

Stents are used in conjunction with balloon catheters in a variety of medical therapeutic applications, including intravascular angioplasty to treat a lesion such as plaque or thrombus. For example, a balloon catheter device is inflated during percutaneous transluminal coronary angioplasty (PTCA) to dilate a stenotic blood vessel. When inflated, the pressurized balloon exerts a compressive force on the lesion, thereby increasing the inner diameter of the affected vessel. The increased interior vessel diameter facilitates improved blood flow. Soon after the procedure, however, a significant proportion of treated vessels restenose.

To reduce restenosis, stents constructed of metals or polymers are implanted within the vessel to maintain lumen size. The stent is sufficiently longitudinally flexible so that it can be transported through the cardiovascular system. In addition, the stent requires sufficient radial strength to enable it to act as a scaffold and support the lumen wall in a circular, open configuration. Configurations of stents include a helical coil, and a cylindrical sleeve defined by a mesh, which may be supported by a stent framework of struts or a series of rings fastened together by linear connecter portions.

Unfortunately, stent insertion can cause undesirable reactions such as inflammation resulting from a foreign body reaction, infection, thrombosis, and proliferation of cell growth that occludes the blood vessel. Polymer coatings applied to the surface of stents have been used to deliver drugs and other therapeutic agents at the placement site of the stent in order to reduce the incidence of deleterious conditions including thrombosis and restenosis.

It would be desirable to provide a biodegradable medical device with hydroxyapatite filaments and/or biodegradable polymer fibers that overcomes the disadvantages described above.

SUMMARY OF THE INVENTION

One aspect of the present invention provides a stent including hydroxyapatite fibers and biodegradable fibers. The hydroxyapatite fibers and biodegradable fibers are interwoven to form the stent lumen.

Another aspect of the invention provides a system of for treating a vascular condition that includes a catheter and a stent disposed on the catheter. The stent includes hydroxyapatite fibers and biodegradable fibers interwoven so that they define the stent lumen.

Yet another aspect of the invention provides a method of manufacturing a stent by forming hydroxyapatite fibers, forming biodegradable fibers, and interweaving the fibers to form a stent lumen.

Yet another aspect of the invention provides a stent including a plurality of hydroxyapatite fibers made solely of hydroxyapatite, with the plurality of hydroxyapatite fibers being interwoven to define a stent lumen.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DETAILED DESCRIPTION

Throughout this specification, like numbers refer to like structures.

The present invention is directed to a system for treating abnormalities of the cardiovascular system including a catheter and a hydroxyapatite stent disposed on the catheter. In one embodiment, the stent includes hydroxyapatite strands or filaments. In another embodiment, the stent includes hydroxyapatite particles embedded in biodegradable polymer filaments.

Hydroxyapatite (HA) has the chemical composition [$Ca_{10}(PO_4)_6(OH)_2$], and is the predominant mineral component of bones and teeth. Crystalline HA is biocompatible and thermodynamically stable under physiological conditions, although generally brittle. Crystalline HA is used extensively as a coating for titanium and polymer implants for orthopedic and dental applications. HA is bioactive, and stimulates collagen and soft tissue growth, and therefore promotes healing. Although thermodynamically stable under physiological conditions, HA is resorbed over time.

Crystalline HA can be produced from calcium and phosphorous compounds by a simple precipitation process. For example, solutions of calcium hydroxide and phosphoric acid are mixed, and heated with stirring. A precipitate of crystalline HA particles that are variable in shape and size forms when the solution returns to room temperature.

Figure 1:
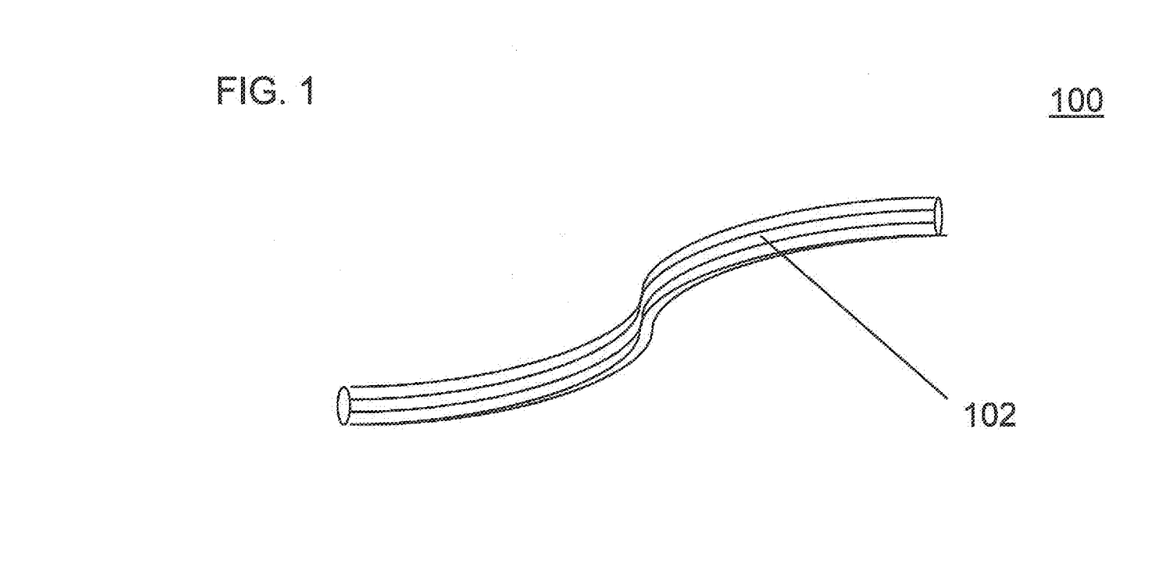
FIG. 1 is a schematic illustration of a hydroxyapatite fiber formed solely of hydroxyapatite filaments, in accordance with the present invention.

FIG. 1 is a schematic illustration of a hydroxyapatite fiber formed solely of hydroxyapatite filaments, in accordance with the present invention. HA fibers 100 have a crystalline structure 102. HA fibers can be produced using a sol-gel process followed by spinning. In this process, two solutions, one of a solubilized calcium (Ca) compound and one of a solubilized phosphorous (P) compound are prepared. The two solutions are mixed with stirring so that a Ca/P ratio of 1.67 is maintained. The resulting solution is heated, and the Ca and P compounds are allowed to react and "age" under carefully controlled conditions of time and temperature until an HA sol, which is a suspension of nano-sized, colloidal particles of HA (having a Ca/P of 1.67), is formed. At this stage of the process, HA can be recovered as nano-particles, such as nano-particles having an exemplary diameter of between about 10 nm and 10 microns. To form HA fibers, water is removed to increase the viscosity and allow the HA to polymerize, resulting in the formation of an HA gel suitable for spinning.

HA fibers made solely of hydroxyapatite are formed by drawing or extruding the viscous HA gel through pores of a defined size. The resulting product consists of HA gel fibers that are collected and calcined at high temperature to remove water and form a final fibrous product 100 having a nanocrystalline HA structure, shown in FIG. 1. Although HA fibers 100 have a crystalline structure 102, the grain size is very small, and they therefore are more flexible, and less brittle than particulate HA. In one example, HA fibers 100 have a diameter between about 2.5 and 15 microns.

Figure 2:
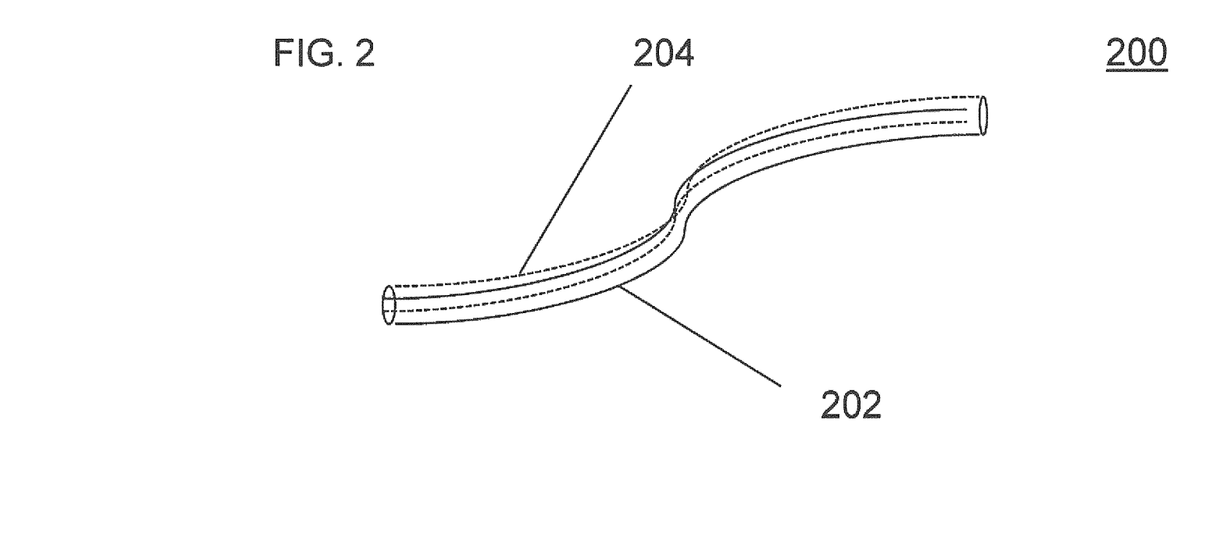
FIG. 2 is a schematic illustration of a hydroxyapatite fiber including hydroxyapatite filaments and biodegradable polymer filaments, in accordance with the present invention.

FIG. 2 is a schematic illustration of a hydroxyapatite fiber including hydroxyapatite filaments and biodegradable polymer filaments, in accordance with the present invention. The hydroxyapatite fiber includes biodegradable polymer filaments and hydroxyapatite filaments spun with biodegradable polymer filaments.

Hydroxyapatite fiber 200 includes HA filaments 202 and poly(lactide-co-glycolide) filaments 204 that are coaxially aligned. A hydroxyapatite fiber 200 including HA and another polymer can be formed by a process known in the art as electrospinning. The HA suspension is mixed with a solution of another polymer and extruded into a voltage field between 10 and 30 kV. The liquid stream becomes charged, and electrostatic forces cause it to elongate and become progressively smaller in diameter. As the liquid stream dries, it becomes a thin, uniform filament having an exemplary diameter of between about 10 and 100 nanometers.

In one embodiment, the polymer that is mixed with the HA suspension is a biocompatible, biodegradable polymer such as hyaluronic acid, polylactic acid, polyglycolic acid, poly(lactide-co-glycolide copolymers, polyamide esters, polyvinyl esters, polyvinyl alcohol, and polyanhydrides. In another embodiment, polymers having shape-memory properties are used. Exemplary shape-memory polymers for use in a self-expanding stent include elastic block copolymers of polyurethane, polyethylene glycol, and ($\xi$-caprolactone)diol.

In one embodiment, a solution of poly(lactide-co-glycolide) copolymer is mixed with an HA suspension in a ratio of between 1:10 and 5:1 by weight. The mixture is then subjected to electrospinning and a hydroxyapatite fiber 200, shown in FIG. 2 is formed. The diameter of hydroxyapatite fiber 200 is determined by the parameters chosen for the electrospinning process. The hydroxyapatite fiber 200 can have an exemplary diameter between about 2.5 and 15 microns.

Figure 3:
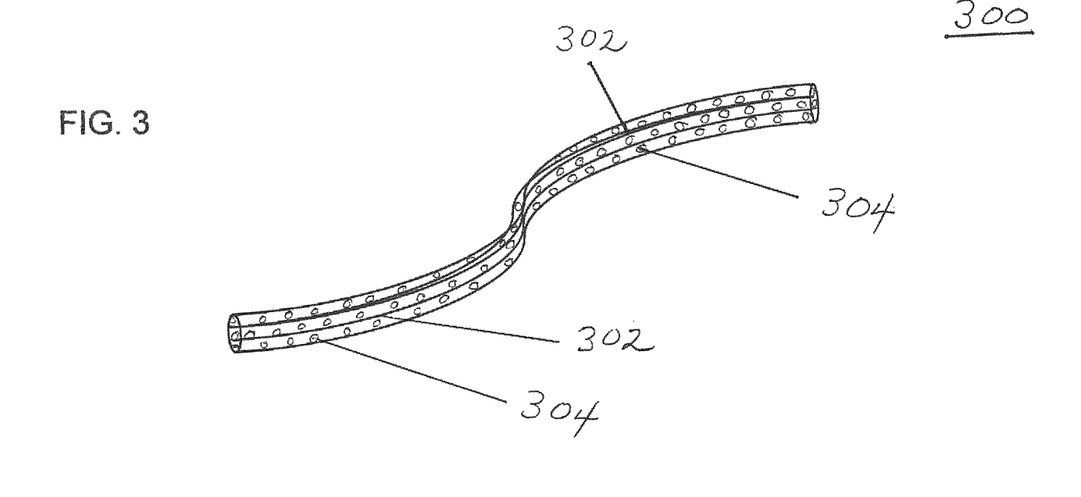
FIG. 3 is a schematic illustration of a hydroxyapatite fiber including hydroxyapatite particles and biodegradable polymer filaments, in accordance with the present invention.

FIG. 3 is a schematic illustration of a hydroxyapatite fiber including hydroxyapatite particles and biodegradable polymer filaments, in accordance with the present invention. The hydroxyapatite fibers include a biodegradable polymer and hydroxyapatite particles dispersed in the biodegradable polymer.

Polymeric filaments and HA particles are combined to form the hydroxyapatite fibers. Filaments are formed from solutions of polymers such as solubilized collagen, or poly(lactide-co-glycolide) by electrospinning and other suitable methods. The polymer filaments are then combined with particles of HA and formed into hydroxyapatite fibers by compression, hot pressing, gel casting, or other techniques known in the art. In one embodiment, the resulting hydroxyapatite fiber 300, shown in FIG. 3, includes filaments 302 of poly(lactide-co-glycolide) that are coaxially aligned along the length of hydroxyapatite fiber 300. Bound within the mesh of filaments 302 are HA particles 304. In one example, HA particles 304 have a diameter between about 10 nm and 10 microns. The ratio within the fibers of hydroxyapatite particles and poly(lactide-co-glycolide) copolymer is between 1:10 and 5:1 by weight.

Figure 4:
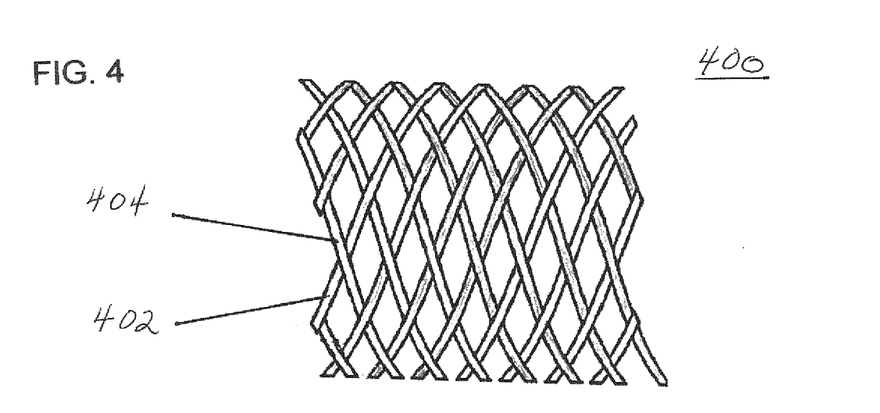
FIG. 4 is a schematic illustration of a portion of a stent wall formed by interweaving hydroxyapatite fibers and biodegradable polymeric fibers, in accordance with the present invention.

FIG. 4 is a schematic illustration of a portion of a stent wall formed by interweaving hydroxyapatite fibers and biodegradable polymeric fibers, in accordance with the present invention. HA fibers can be combined with biodegradable polymeric fibers to form medical devices such as stents, stent grafts, and other grafts that provide therapeutically beneficial properties. The polymer and HA content are selected to provide the mechanical characteristics needed for each particular application. The fibers can be interwoven by hand or mechanically to form stent wall 400. Woven stent wall 400 may be prepared as a flat sheet, and then rolled into a tubular shape.

In one embodiment, shown in FIG. 4, stent wall 400 is formed by interweaving HA fibers 402 with biodegradable polymeric fibers 404. In another embodiment, stent wall 400 includes only a number of interwoven HA fibers made solely of hydroxyapatite.

In another embodiment, HA fibers 402 are HA particles dispersed in a biodegradable polymer. HA fibers 402 can include HA particles having an exemplary diameter between about 10 nm and 10 microns bound to poly(lactide-co-glycolide) filaments. The ratio of hydroxyapatite particles and poly(lactide-co-glycolide) copolymer can be between about 1:10 and 5:1 by weight. The polymer composition and HA content are selected to provide desired physical and mechanical characteristics including flexibility, tensile strength and elastic modulus.

Figure 5:
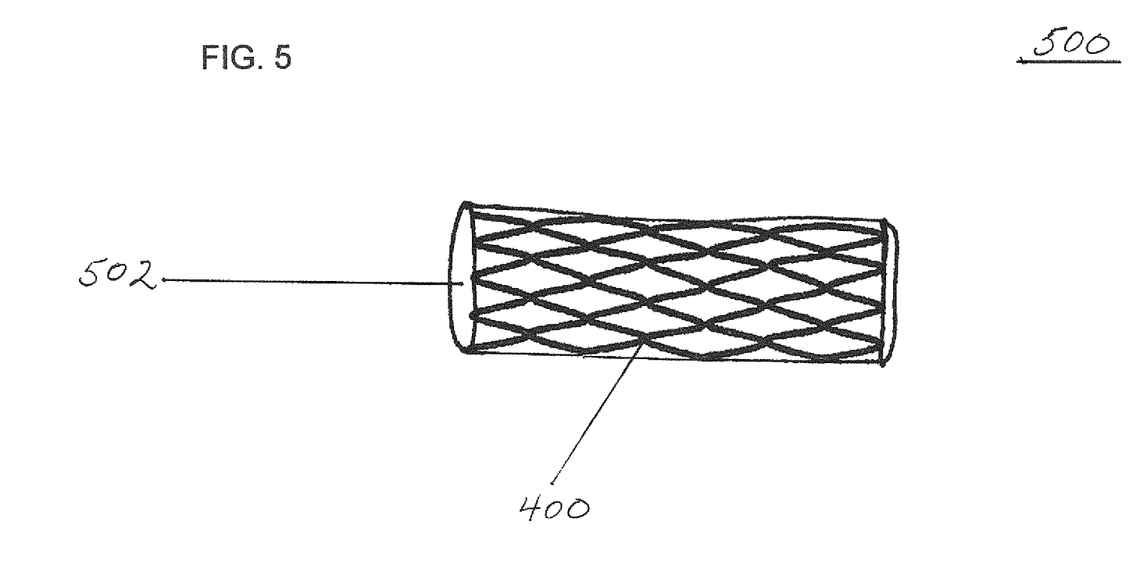
FIG. 5 is a schematic illustration of a stent having a stent lumen defined by interwoven hydroxyapatite fibers and biodegradable fibers, in accordance with the present invention.

FIG. 5 is a schematic illustration of a stent having a stent lumen defined by interwoven hydroxyapatite fibers and biodegradable polymeric fibers, in accordance with the present invention. The woven stent wall 400 may be rolled into a tubular shape to form expandable stent 500 shown in FIG. 5. Alternatively, the fibers can be mechanically woven around a cylindrical form into a tubular structure; the tubular structure is then cut to a desired length to form stent 500. In the resulting stent 500, the woven fibrous wall 400 defines stent lumen 502.

Stent 500 is flexible and expandable, and can be mounted on a catheter and delivered to a treatment site within the vascular system. The stent 500 includes hydroxyapatite fibers and biodegradable polymeric fibers, or hydroxyapatite fibers alone, which are interwoven to define a stent lumen. The stent 500 can be balloon expandable or self-expanding. When the stent 500 is balloon expandable, the system for treating a vascular condition includes a catheter; a balloon disposed on the catheter; and stent 500 disposed on the balloon. Those skilled in the art will appreciate that in other embodiments the stent can be self-expanding, so that the balloon can be omitted. When the stent 500 is self-expanding, it can be delivered to the treatment site on a catheter without a balloon. The catheter can include a retractable sheath to restrain the self-expanding stent until the stent reaches the deployment site.

At the treatment site, the stent is positioned across the lesion to be treated, and expanded, either with a balloon or through self-expansion. The catheter is then withdrawn from the body. Once positioned at the treatment site, the stent provides support for the vessel wall and maintains vessel patency. In addition, the HA in stent wall 400 promotes tissue ingrowth and healing at the treatment site. After stent placement, the biodegradable polymer breaks down and is removed from the site, and the HA is resorbed, leaving the treatment site healed.

Figure 6:
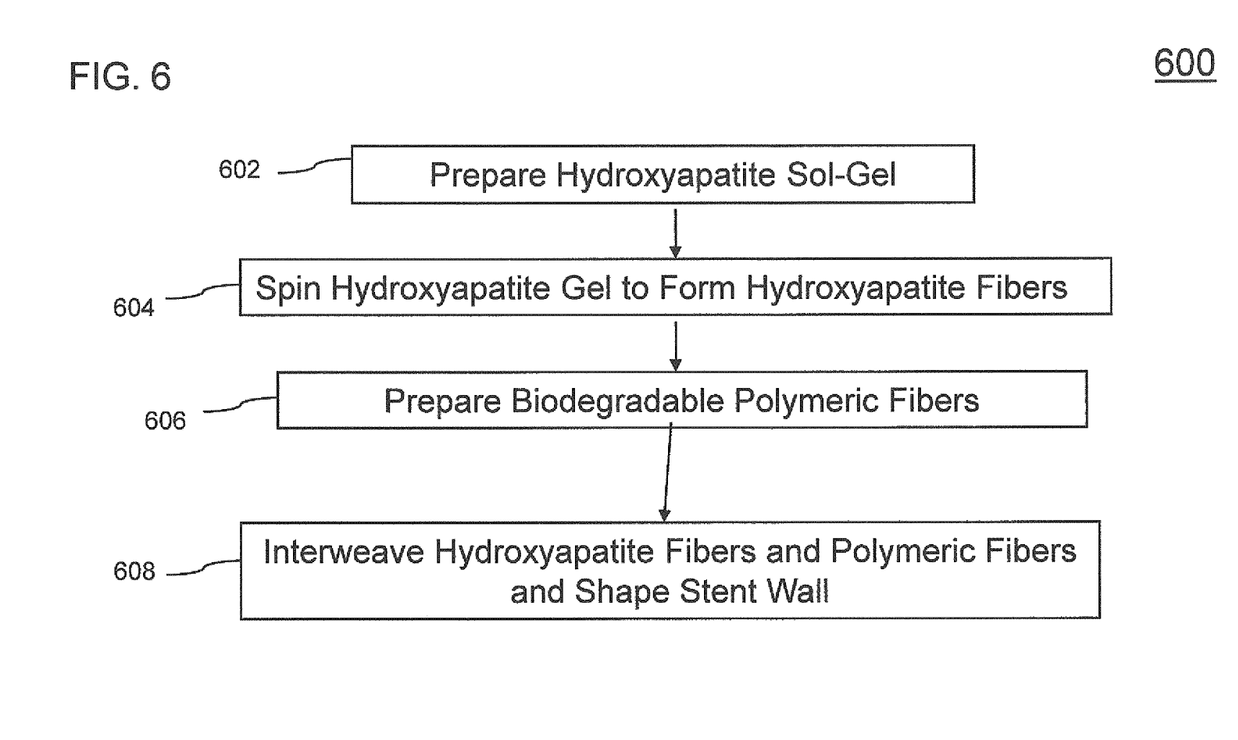
FIG. 6 is a flow diagram for a method of manufacturing a woven stent including hydroxyapatite fibers and biodegradable fibers, in accordance with the present invention.

FIG. 6 is a flow diagram for a method of manufacturing a woven stent including hydroxyapatite fibers and biodegradable fibers, in accordance with the present invention. The method of manufacturing a stent includes forming hydroxyapatite fibers; forming biodegradable polymeric fibers; and interweaving the hydroxyapatite fibers with the biodegradable polymeric fibers to define a stent lumen.

FIG. 6 illustrates a one method of manufacturing stent 500 including HA fibers. First, a sol-gel of HA is prepared, as shown in Block 602. Calcium and phosphate compounds, in a Ca/P ratio of 1.67 are dissolved and allowed to react to form nano-sized particles of HA. Water is then removed and the sol becomes viscous and forms a gel that is suitable for spinning. Next, the HA gel is spun, as shown in Block 604, by extruding the gel through pores of a defined size. The resulting HA fibers can then heated to form a nano-crystalline structure. Biodegradable polymeric fibers are prepared, as shown in Block 606, by compression, gel casting, electrospinning, or other appropriate methods. Finally, the HA fibers and the biodegradable polymeric fibers are interwoven and shaped into a stent wall that defines the stent lumen, as shown in Block 608. Further detail on the formation and specifics of the hydroxyapatite fibers is provided in the description of FIGS. 1-3 above.

While the invention has been described with reference to particular embodiments, it will be understood by one skilled in the art that variations and modifications may be made in form and detail without departing from the spirit and scope of the invention.

The invention claimed is:

1. A stent consisting of:
   hydroxyapatite fibers, the hydroxyapatite fibers consisting of biodegradable polymer filaments coaxially aligned in a mesh along the length of the hydroxyapatite fibers and hydroxyapatite particles bound within the mesh; and
   biodegradable polymeric fibers;
   wherein the hydroxyapatite fibers and biodegradable polymeric fibers are interwoven to define a stent lumen.

2. The stent of claim 1 wherein the diameter of the hydroxyapatite particles is between 10 nm and 10 microns.

3. The stent of claim 1 wherein the hydroxyapatite fibers have a diameter between 2.5 and 15 microns.

4. The stent of claim 1 wherein the biodegradable polymeric fibers are formed of a biodegradable polymer selected from the group consisting of hyaluronic acid, polylactic acid, polyglycolic acid, poly(lactide-co-glycolide copolymers, polyamide esters, polyvinyl esters, polyvinyl alcohol, polyanhydrides, and elastic block copolymers of polyurethane, polyethylene glycol, and (ξ-caprolactone)diol.

5. The stent of claim 1 wherein the biodegradable polymer filaments are formed of collagen.

6. A system for treating a vascular condition comprising:
   a catheter; and
   a stent disposed on the catheter;
   wherein the stent consists of hydroxyapatite fibers and biodegradable polymeric fibers, the hydroxyapatite fibers and biodegradable polymeric fibers being interwoven to define a stent lumen, the hydroxyapatite fibers consisting of biodegradable polymer filaments coaxially aligned in a mesh along the length of the hydroxyapatite fibers and hydroxyapatite particles bound within the mesh.

7. The system of claim 6 wherein the diameter of the hydroxyapatite particles is between 10 nm and 10 microns.

8. The system of claim 6 wherein the hydroxyapatite fibers have a diameter between 2.5 and 15 microns.

9. The system of claim 6 wherein the catheter includes a balloon and the stent is disposed on the balloon.

10. The system of claim 6 wherein the biodegradable polymer filaments are formed of collagen.

\* \* \* \* \*